United States Patent [19]

Itaya et al.

[11] 4,241,220
[45] Dec. 23, 1980

[54] PROCESS FOR PRODUCING TEREPHTHALIC ACID

[75] Inventors: Shikiho Itaya, Ohtake; Takenori Nagaoka; Teruo Itoh, both of Iwakuni; Yukimasa Shigemura, Ohtake; Shigemi Shiraki, Iwakuni, all of Japan

[73] Assignee: Mitsui Petrochemical Industries, Ltd., Tokyo, Japan

[21] Appl. No.: 973,944

[22] Filed: Dec. 28, 1978

[30] Foreign Application Priority Data

Dec. 28, 1977 [JP] Japan ................................. 52-157225
Dec. 28, 1977 [JP] Japan ................................. 52-157226
Dec. 28, 1977 [JP] Japan ................................. 52-157227

[51] Int. Cl.$^3$ .............................................. C07C 51/16
[52] U.S. Cl. ................................... 562/414; 562/416; 562/485
[58] Field of Search ......................... 562/414, 485

[56] References Cited

FOREIGN PATENT DOCUMENTS 47-20141  6/1972  Japan .
1511181   5/1978  United Kingdom .

*Primary Examiner*—A. Siegel
*Attorney, Agent, or Firm*—Sherman & Shalloway

[57] ABSTRACT

Improved process for producing terephthalic acid by liquid-phase catalytic oxidation of p-xylene with oxygen at a temperature of at least about 160° C. and a pressure of at least about 5 kg/cm²G under specific recycling condition of the mother liquor, which comprises (A) performing said liquid-phase catalytic oxidation at a temperature (T) within the range of about 170° C. to about 230° C. to form an oxidation reaction mixture containing crude terephthalic acid having a 4-carboxybenzaldehyde content of 500 to 3,000 ppm and an optical density, measured at 340 mµ, of not more than 0.3, (B) separating about 60 to about 98% by weight of the total mother liquor from the resulting oxidation reaction mixture at a temperaure of from (T−30)° C. to (T+10)° C., and recycling the separated mother liquor to the oxidation zone, (C) adding hot acetic acid to the remainder of the oxidation reaction mixture so that the weight ratio of acetic acid to crude terephthalic acid in the product is 2:1 to 10:1 to form a suspension of the crude terephthalic acid in acetic acid kept at a temperature ranging from the reaction temperature (T) to about 240° C., (D) stirring the suspension at a temperature of from T°C. to about 240° C. to perform a primary leaching treatment, (E) stirring the treated suspension at a temperature of 150° C. to about 220° C., said temperature being at least 10° C. lower than the temperature of the primary leaching treatment, thereby to perform a secondary leaching treatment, and (F) recovering terephthalic acid from the suspension subjected to the secondary leaching treatment.

14 Claims, 1 Drawing Figure

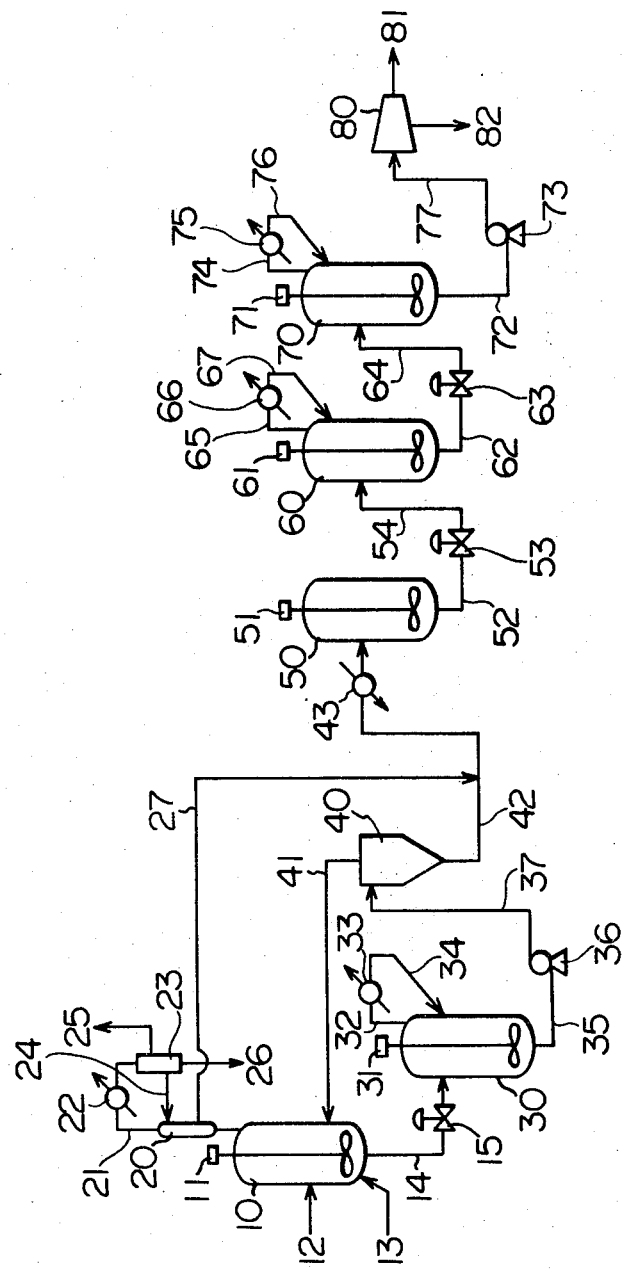

PROCESS FOR PRODUCING TEREPHTHALIC ACID

This invention relates to an improved process for producing with good quality reproducibility terephthalic acid of high quality which can be advantageously used in the production of polyesters by a direct polymerization method which, for example, involves directly esterifying terephthalic acid with ethylene glycol and subsequently polycondensing the ester. Specifically, the invention relates to a process for producing terephthalic acid, which has a size and a configuration suitable for the preparation of a slurry of good pumpability or flowability together with ethylene glycol and which can give a polyester of good color with good quality reproducibility by a direct polymerization method, by one-step liquid-phase catalytic oxidation of p-xylene without the need for a complicated and expensive purifying procedure and with reduced decomposition of acetic acid solvent.

More specifically, this invention provides a process for producing terephthalic acid by oxidizing p-xylene with a molecular oxygen-containing gas in an acetic acid solvent in the presence of a catalyst containing a cobalt compound, a manganese compound and a bromine compound at a temperature of at least about 160° C. and a pressure of at least about 5 kg/cm² (gauge) in an oxidation zone, recycling a part of the mother liquor in the resulting oxidation reaction mixture to the oxidation zone, leaching the remainder of the oxidation reaction mixture with acetic acid, and recovering terephthalic acid from the treated mixture; which comprises (A) performing said liquid-phase catalytic oxidation at a temperature (T) within the range of about 170° C. to about 230° C. to form an oxidation reaction mixture containing crude terephthalic acid having a 4-carboxybenzaldehyde content of 500 to 3,000 ppm, preferably 600 to 2,500 ppm and an optical density, measured at 340 mμ, of not more than 0.3, preferably not more than 0.2, (B) separating about 60 to about 98% by weight, preferably about 60 to about 95% by weight, of the total mother liquor from the resulting oxidation reaction mixture at a temperature of from (T−30)° C. to (T+10)° C., preferably from (T−20)° C. to T° C., and recycling the separated mother liquor to the oxidation zone, (C) adding hot acetic acid to the remainder of the oxidation reaction mixture so that the weight ratio of acetic acid to crude terephthalic acid in the mixture is 2:1 to 10:1, preferably 3:1 to 8:1, to form a suspension of the crude terephthalic acid in acetic acid kept at a temperature ranging from the reaction temperature (T) to about 240° C., preferably from (T+10)° C. to about 230° C., (D) stirring the suspension at a temperature of from T° C. to about 240° C. to perform a primary leaching treatment, (E) stirring the treated suspension at a temperature of 150° C. to about 220° C., preferably about 160° C. to about 200° C., said temperature being at least 10° C., preferably at least about 20° C., lower than the temperature of the primary leaching treatment, thereby to perform a secondary leaching treatment, and (F) recovering terephthalic acid from the suspension subjected to the secondary leaching treatment.

A widely used conventional process for producing terephthalic acid comprises oxidizing p-xylene with a molecular oxygen-containing gas in an acetic acid solvent in the presence of a heavy metal-containing oxidation catalyst. Various methods have been suggested for producing terephthalic acid by this one-step oxidation reaction which has a high enough quality to be usable in the production of polyesters by a direct polymerization method. With these methods, however, such high quality terephthalic acid are difficult to produce economically by easy operations. For example, production of such high quality terephthalic acid by one-step oxidation reaction have operational and equipment disadvantages because it must be effected under severe oxidation conditions having regard to the proportion of the solvent, the composition of the catalyst, the reaction temperature, the amount of the molecular oxygen-containing gas (the content of oxygen in the exhaust gas) and the residence time. These severe reaction conditions result in markedly increased oxidative decomposition of the acetic acid solvent, and therefore, terephthalic acid of high quality cannot be produced economically.

It has been the usual practice therefore to produce crude terephthalic acid containing fairly large amounts of impurities such as oxidation intermediates (e.g., 4-carboxybenzldehyde) and colored substances without employing such severe reaction conditions, and then to subject it to a purifying treatment such as catalytic hydrogenation, catalytic decarbonylation or recrystallization to form terephthalic acid of improved quality. Such a method, however, has the disadvantage that the purifying treatment is complicated, and a purifying apparatus must be additionally provided. This naturally leads to the increased cost of production. Terephthalic acid so purified, therefore, does not fully meet the requirements of terephthalic acid for direct polymerization in regard to operation, equipment and economy.

In an attempt to avoid the aforesaid disadvantages and to provide terephthalic acid of improved quality, it was also suggested to recycle a part of the mother liquor in the liquid-phase catalytic oxidation reaction mixture to the oxidation reaction zone, leaching the remainder of the oxidation reaction mixture with acetic acid, and recovering terephthalic acid from the treated mixture. For example, U.S. Pat. No. 3,364,256 discloses a process for the preparation of a high purity terephthalic acid which comprises the steps of suspending 6 to 100 parts by weight of a crude terephthalic acid separated from a reaction mixture which has been obtained by oxidation of a p-dialkylbenzene such as p-xylene with molecular oxygen in a liquid medium in the presence of a cobaltic compound, in 100 parts by weight of at least one alkanoic acid having 2 to 4 carbon atoms such as acetic acid and having a total water content of less than 50% by weight, heating the suspension at a temperature in the range of 180° to 230° C. under conditions such that at least 50% by weight of the fed crude terephthalic acid may be present in the form of a solid phase, and thereafter separating terephthalic acid. In this suggestion, Co(III) is used as a catalyst, and a manganese compound and a bromine compound are not used. It is essential in this process to separate the crude terephthalic acid from the oxidation reaction mixture, again suspend it in a liquid medium such as acetic acid, and heat the suspension to the temperature described above. The process is therefore disadvantageous in regard to operation and economy of heat energy. The process also requires a large quantity of a purifying medium. The cited U.S. Patent does not disclose the recycling of a part of the mother liquor in the oxidation reaction mixture to the oxidation reaction zone. The terephthalic acid obtained by this process has a relatively small particle size and is not spherical in shape. Thus, the shape and particle size are not suitable for forming a slurry of good pumpability with ethylene glycol in the direct polymerization method. The resulting terephthalic acid also contains an unneglible amount of by-product 4-carboxybenzldehyde. Hence, the process of this U.S. Patent does not produce satisfactory results.

A technique of avoiding the disadvantages of the above-cited U.S. Patent and obtaining a better purifying effect more advantageously was suggested in Japanese Laid-Open Patent Publication No. 20141/74 (published on Feb. 22, 1974). In this suggestion, too, Co(III) is used as a catalyst, and no manganese and bromine compounds are used. In this technique, crude terephthalic acid is separated from the oxidation reaction mixture, and subjected to a two-stage leaching treatment instead of the one-stage leaching treatment in the aforesaid U.S. Patent. Specifically, 6 to 100 parts by weight of the crude terephthalic acid so separated is suspended in 100 parts by weight of a $C_2$–$C_4$ aliphatic monocarboxylic acid such as acetic acid having a water content of not more than 50% by weight. The suspension is heated at 180° to 260° C. under conditions such that at least 50% by weight of the terephthalic acid charged is present as a solid phase. The heat-treated suspension is then fed into one or more vessels connected in series so that the temperature therein decreases progressively as the vessels are located more downstream. During this time, terephthalic acid is crystallized, and the pressure in the vessels is made to progressively approach the atmospheric pressure by adjusting the amount of the medium adiabatically evaporated in each vessel to 0.05 to 0.6 times the weight of the medium fed. Thus, the crystallized terephthalic acid is obtained. In the Examples of this Japanese Publication, even the lowest content of by-product 4-carboxybenzaldehyde is as high as 5700 ppm. Hence, the resulting terephthalic acid is unsatisfactory for use in direct polymerization.

The 4-carboxybenzldehyde content of terephthalic acid obtained by the present invention, as will be shown in Examples to be given hereinbelow, is as small as about 130 to about 400 ppm. Furthermore, as shown in Comparative Example 14 to be given hereinbelow, when an oxidation reaction mixture obtained by using a Co(III) catalyst disclosed in this Japanese Publication at reaction temperatures which are conventional in regard to this catalyst and utilized in this Publication is subjected to the two-stage leaching treatment, satisfactory results cannot be obtained.

Belgian Pat. No. 840,624 (corresponding to British Pat. No. 1,511,181) discloses a process for preparing terephthalic acid by liquid-phase oxidation in the presence of a catalyst comprising a cobalt compound, a manganese compound and a bromine compound as in the present application, wherein the crude terephthalic acid is subjected to a leaching treatment. According to this process, an oxidation reaction mixture containing crude terephthalic acid obtained by oxidizing p-xylene with a molecular oxygen-containing gas at 160° to 180° C. in the presence of a catalyst comprising a cobalt compound, a manganese compound and a bromine compound is held at a temperature from 50° C. below to 25° C. above the oxidation reaction temperature without separating the mother liquor, and then terephthalic acid is separated. The separated terephthalic acid is slurried in the mother liquor or in fresh acetic acid solvent. The slurry is held at a temperature of at least 100° C., specifically up to about 160° C., and then the terephthalic acid is separated. It is stated in the patent that according to this process, the oxidative decomposition of acetic acid can be inhibited, and terephthalic acid usable in a direct polymerization method can be produced.

Since in the process of the Belgian Patent, the oxidation reaction mixture is held at the aforesaid temperature without separating the mother liquor from it, a sufficient purifying effect cannot be expected. A satisfactory leaching effect is difficult to obtain by separating terephthalic acid after the above hold-up, slurring it, and holding the slurry again at a temperature of at least 100° C. The resulting terephthalic acid contains large amounts of colored impurities other than 4-carboxybenzaldehyde and other impurities such as toluic acid, and has a high optical density. Accordingly, polyethylene terephthalate of good color cannot be obtained from this terephthalic acid by a direct polymerization method, as is clearly seen from Example 15 of this Belgian Patent. Furthermore, since the terephthalic acid obtained by this method is in the form of pillar-like or needlelike crystals, a slurry of it formed together with ethylene glycol does not possess good pumpability in a direct polymerization method. This will be readily understood from the results of Comparative Example 15 given hereinbelow which was performed under the conditions shown in Example 16 of this Belgian Patent in which the amount of by-product carboxybenzaldehyde is the smallest among the Examples in the Belgian Patent.

The present inventors made investigations in order to develop a commercially advantageous process for oxidizing p-xylene in a single step with reduced oxidative decomposition of acetic acid solvent so as to provide terephthalic acid of high purity suitable for use as a raw material for the production of polyesters by the direct polymerization method.

High purity and good color are not enough as requirements of terephthalic acid for use in the production of polyesters by the direct polymerization method. In the direct polymerization method, it is essential that terephthalic acid should be mixed with a substantially equimolar amount of ethylene glycol and reacted in suspension. In such a solid-liquid heterogeneous reaction system, a slurry of the starting terephthalic acid and ethylene glycol is required to have good flowability or pumpability during mixing with stirring or during transportation. To increase the pumpability of a suspension of high purity terephthalic acid in ethylene glycol, it is necessary that the crystals of terephthalic acid should be nearly spherical, and have a large average particle diameter. Accordingly, terephthalic acid used in the production of polyesters by direct polymerization is required to give a slurry of good pumpability with ethylene glycol in addition to having high purity and good color.

It is moreover desirable to develop a process by which high purity, good color and good pumpability can be achieved commercially advantageously and with good reproducibility of product quality without requiring a complicated and expensive purifying means or causing the decomposition of acetic acid solvent.

The investigations of the present inventors led to the discovery that the 4-carboxybenzaldehyde content of crude terephthalic acid obtained by the liquid-phase oxidation of p-xylene with a molecular oxygen-containing gas is in a contradictory relationship with the percent decomposition of acetic acid solvent, in other words avoiding the formation of undesirable 4-carboxybenzaldehyde and avoiding the undesirable decomposition of acetic acid solvent are difficult to achieve simultaneously; and that there is a correlation among the 4-carboxybenzaldehyde content of the crude terephthalic acid, the optical density of an alkaline aqueous solution of the crude terephthalic acid, and the leaching treatment effect of the crude terephthalic acid.

It has also been found that the oxidative decomposition of acetic acid solvent can be inhibited positively by oxidizing p-xylene catalytically in the liquid phase under comparatively mild oxidation conditions to form an oxidation reaction mixture containing crude terephthalic acid with fairly large amounts of impurities such as 4-carboxybenzaldehyde; and that when the resulting crude terephthalic acid contains 500 to 3,000 ppm of 4-carboxybenzaldehyde and has an optical density at 340 m$\mu$, which is a measure for the content of colored impurities, of not more than 0.3, high quality terephthalic acid in the form of spherical particles with a large particle diameter which gives a slurry of good pumpability with ethylene glycol and can be used for the production of polyesters by the direct polymerization method can be produced by substituting a specified amount of hot acetic acid for mother liquor in the oxidation reaction mixture without so much cooling the reaction mixture, and subjecting the resulting suspension containing the crude terephthalic acid to a two-step leaching treatment at a specified temperature.

The new findings described above led to the discovery that high quality terephthalic acid meeting the aforesaid requirements can be prepared under a combined set of the conditions (A), (B), (C), (D), (E) and (F) of the invention described hereinabove in a process for producing terephthalic acid which comprises oxidizing p-xylene in the liquid phase with a molecular oxygen-containing gas such as air in acetic acid solvent in the presence of a catalyst comprising a cobalt compound, a manganese compound and a bromine compound at a temperature of at least about 160° C. and a pressure of at least about 5 kg/cm$^2$ (gauge) in an oxidation zone, recycling a part of the mother liquor in the resulting oxidation reaction mixture to the oxidation zone, and separating the remainder of the oxidation reaction mixture.

It has also been found that conditions for stirring the suspension in the primary leaching treatment (D) and the secondary leaching treatment (E) affects the production of high quality terephthalic acid with good reproducibility of quality, and the use of appropriate stirring conditions makes it possible to achieve good reproduction of quality. It has been found that better results can be obtained when in step (D), stirring is performed under such conditions that the stirring power per cubic meter of the suspension is at least 1 HP, preferably 1.3 to 4 HP, and the linear velocity of the tip of a stirring blade of the stirrer is at least 0.8 m/sec., preferably 1.3 to 5 m/sec., and in step (E), the stirring is performed under such conditions that the stirring power per cubic meter of the suspension is 1 to 5 HP, preferably 1.3 to 3 HP, and the linear velocity of the tip of a stirring blade of the stirrer is 0.8 to 4 m/sec, preferably 1.3 to 3 m/sec.

It has also been found unexpectedly that even when terephthalic acid obtained by the process of the invention meeting the requirements (A), (B), (C), (D), (E) and (F) has a higher 4-carboxybenzaldehyde content and a higher optical density at 340 m$\mu$ than high purity terephthalic acids which, for example, have a 4-carboxybenzaldehyde content of less than 300 ppm and an optical density at 340 m$\mu$ of less than 0.05, and have previously been considered to be usable in a direct polymerization method, it can be used to form a polyester of good color by the direct polymerization method.

It is an object of this invention therefore to provide an improved process for preparing high quality terephthalic acid having high purity, good color and good slurry pumpability with good reproducibility of quality by commercially advantageous operations while avoiding the undesirable consumption of acetic acid solvent.

The above and other objects and advantages of the invention will become more apparent from the following description.

The catalyst used in this invention is any known oxidation catalyst capable of generating a cobalt ion, a manganese ion and a bromine ion in the liquid phase catalytic oxidation zone. Usually, an oxidation catalyst composed of a cobalt compound, a manganese compound and a bromine compound is used. It may contain other catalytic metal ingredients in addition to the three essential ingredients, cobalt, manganese and bromine compounds. The amount of the oxidation catalyst composed of cobalt, manganese and bromine compounds used in the invention is not particularly limited. Preferably, the amount of the cobalt compound, determined as cobalt atom, is $0.1 \times 10^{-5}$ to $5.0 \times 10^{-5}$ per gram of the acetic acid solvent; the amount of the manganese compound is such that the atomic ratio of the manganese compound to the cobalt compound is within the range of 0.001 to 1.0; and the amount of the bromine compound is such that the atomic ratio of bromine to the sum of cobalt and manganese atoms is within the range of 1 to 4.

The acetic acid solvent used in the liquidphase catalytic oxidation reaction in accordance with the process of this invention needs not to be of pure acetic acid, and for example, acetic acid containing about 5 o about 15% by weight of water can be used. The amount of the acetic acid solvent is such that the weight ratio of it to p-xylene is within the range of from about 2 to about 10, preferably from about 3 to about 6. The water content of the mother liquor in the reaction system of oxidation reaction is, for example, about 5 to about 15% by weight, preferably about 7 to about 12% by weight, The molecular oxygen-containing gas used in the process of this invention is usually air. It may be an oxygen gas, or a mixture of it with an inert gas such as nitrogen in any desired mixing ratios. The amount of the molecular oxygen-containing gas to be fed into the oxidation zone is suitably such that the oxygen concentration of the exhaust gas from the oxidation zone is about 2 to about 8%, preferably about 3 to 6% by weight.

In the process of this invention, p-xylene is oxidized at elevated temperatures and pressures. The reaction temperature (T) should be about 170 to about 230° C., preferably about 180° to about 220° C. If the oxidation reaction temperature is lower than about 170° C., the oxidation reaction is incomplete. Consequently, the 4-carboxybenzaldehyde content of the crude terephthalic acid increases beyond the upper limit specified in requirement (A) in the process of this invention. Moreover, owing to impurities considered to be ascribable to the incompleteness of the oxidation reaction, the optical density at 340 mµ of the crude terephthalic acid increases beyond the upper limit specified in requirement (A) in the process of the invention. If an oxidation reaction mixture containing crude terephthalic acid not meeting the requirement (A) is used, the purifying effect in the leaching treatment steps (D) and (E) of the process of this invention is reduced markedly, and it is impossible to obtain terephthalic acid of high quality which can be used in a direct polymerization method.

When the oxidation reaction temperature is higher than 230° C., oxidation becomes too vigorous to give unidentifiable by-product impurities which cannot be assessed by the 4-carboxybenzaldehyde content and optical density at 340 mµ of crude terephthalic acid. Even when the crude terephthalic acid at such a high oxidation temperature has an optical density at 340 mµ of not more than 0.3, it cannot be purified to high quality terephthalic acid capable of producing polyesters of good quality by subjecting it to the two-step leaching treatment in accordance with this invention. This is presumably because the aforesaid unidentifiable impurities cannot be removed by the leaching treatment. Moreover, at such high oxidation temperatures, the oxidative decomposition of the acetic acid solvent increases.

The pressure at which the liquid-phase catalytic oxidation of p-xylene is performed in the process of this invention is any desired pressure sufficient to maintain the oxidation reaction mixture in the reaction zone in the liquid phase. Usually, it is at least about 5 kg/cm$^2$ (gauge), preferably about 6 to about 30 kg/cm$^2$(gauge), more preferably about 7 to about 15 kg/cm$^2$(gauge). When the oxidation reaction is carried out while removing byproduct water by distillation using an oxidation reactor having a distillation tower fitted to its top portion as will be described hereinbelow, the reaction pressure is maintained within the range in which the boiling of the reaction solvent can be maintained.

The liquid-phase catalytic oxidation reaction is preferably carried out with stirring. Preferably, the stirring is performed under conditions which are convenient for rendering the undesirable impurities in crude terephthalic acid readily removable by the subsequent leaching treatment and for inhibiting the decomposition of acetic acid in the oxidation reaction. To meet such conditions, the intensity of stirring is preferably within the range of about 1 to about 10 HP, especially about 1.5 to about 5 HP, per cubic meter of the oxidation reaction mixture.

For the liquid-phase catalytic oxidation reaction, an oxidation reactor of normal type having a reflux condenser connected to its top portion which is capable of condensing vaporized acetic acid solvent and refluxing it to the reactor, and an oxidation reactor having a distillation tower connected to its top portion can be used. The latter is preferred because the byproduct water can be removed out of the reaction system easily by distillation utilizing the heat of reaction, and the concentration of water in the mother liquor within the reaction system can be controlled easily within a suitable range.

It is essential that the oxidation reaction mixture obtained by the liquid-phase catalytic oxidation of p-xylene should contain crude terephthalic acid having a 4-carboxbenzaldehyde content of 500 to 3,000 ppm and an optical density at 340 mµ of not more than 0.3. To reduce the 4-carboxybenzaldehyde of crude terephthalic acid contained in the oxidation reaction mixture to below 500 ppm, it would be necessary to render the oxidation reaction conditions more severe by increasing the amount of the acetic acid solvent based on the p-xylene, the oxidation reaction temperature, the concentration of the catalyst or the amount of the molecular oxygen-containing gas fed, changing the composition of the catalyst, or by decreasing the concentration of water in the mother liquor within the reaction system. As a result, the impurities change in quality, and even when the oxidation reaction mixture is purified by the two-step leaching treatment in accordance with this invention, it is difficult to obtain terephthalic acid having such a high quality as will give polyesters of good color by the direct polymerization method. Moreover, under such severe conditions, the oxidative decomposition of the acetic acid solvent increases abruptly, and terephthalic acid cannot be produced economically. To avoid such disadvantages, the 4-carboxybenzaldehyde content of the crude terephthalic acid contained in the oxidation reaction mixture should be adjusted to at least 500 ppm. On the other hand, if the 4-carboxybenzaldehyde content of the crude terephthalic acid contained in the oxidation reaction mixture is more than 3000 ppm, impurities other than 4-carboxybenzaldehyde ascribable to reaction intermediates abruptly increase. Even when such an oxidation reaction mixture is subjected to the steps (B) to (E) of the process of this invention, the purifying effect decreases drastically, and it is difficult to obtain terephthalic acid having such a high quality as can give polyethylene terephthalate of good quality by the direct polymerization method.

In addition to the specified 4-carboxybenzaldehyde content, the crude terephthalic acid obtained in (A) should also have an optical density at 340 mµ of not more than 0.3. If its optical density is larger than 0.3, terephthalic acid of such a high quality as will give polyesters by the direct polymerization method cannot be obtained by the primary leaching treatment (D) and the subsequent secondary leaching treatment (E) even when it has the above-specified 4-carboxybenzaldehyde content.

Thus, especially preferably, the crude terephthalic acid contained in the oxidation reaction mixture has a 4-carboxybenzaldehyde content of 600 to 2,500 ppm, and an optical density at 340 mµ of not more than 0.2

In determining the 4-carboxybenzaldehyde content of crude terephthalic acid in the oxidation reaction mixture obtained by this invention, the sample is prepared by cooling the oxidation reaction mixture from the oxidation reactor, separating the precipitated crude terephthalic acid by filtration, washing it with acetic acid and water at room temperature, and drying it. The 4-carboxybenzaldehyde content of the sample is then measured by polarography.

In determining the optical density of the crude terephthalic acid, 7.5 g of the crude terephthalic acid is dissolved in 50 ml of a 2N aqueous solution of potassium hydroxide, and the optical density of the solution is measured at 340 mµ using a 1 cm-long cell.

In the present invention, oxidation reaction conditions such as the ratio of acetic acid solvent to pxylene, the composition of the catalyst, the concentration of the catalyst, the concentration of water in the mother liquor within the reaction system, the amount of the molecular oxygen-containing gas to be fed (the concentration of oxygen gas in the exhaust gas), and the intensity of stirring are suitably selected while the oxidation reaction temperature (T) is within the range of from about 170° C. to about 230° C. to form an oxidation reaction mixture containing crude terephthalic acid having the specified 4-carboxybenzaldehyde content and optical density. A part of the mother liquor separated under the condition specified in (B) is recycled to the oxidation reaction zone.

Separation of the mother liquor from the oxidation reaction mixture should be performed without cooling the product to a temperature which is more than 30° C. below the oxidation reaction temperature (T). Usually, this separation procedure is effected at a temperature of from (T−30)° C. to (T+10)° C., and preferably from (T−20)° C. to T° C. The proportion of the mother liquor to be separated from the oxidation reaction mixture should be about 60% by weight to 98% by weight, preferably about 60 to about 95% by weight, based on the total weight of the mother liquor in the oxidation reaction mixture.

If the separation of the mother liquor from the oxidation reaction mixture is performed at a temperature lower than (T−30)° C., 4-carboxybenzaldehyde and colored impurities contained in the mother liquor are occluded by the crude terephthalic acid, and the 4-carboxybenzaldehyde content of the crude terephthalic acid increases and its optical density at 340 m$\mu$ becomes higher. Consequently, it exerts an increased load on the purification of the crude terephthalic acid in the primary leaching treatment step (D). Moreover, the separated mother liquor must be heated again in recycling to the oxidation zone, and the remainder of the oxidation reaction mixture, after formation of a suspension in step (C), must be again heated prior to the primary leaching treatment step (D). Accordingly, the separation at such a low temperature is uneconomical in regard to the amount of heat used.

When the proportion of the mother liquor separated from the oxidation reaction mixture is decreased to below 60% by weight, impurities such as 4-carboxybenzaldehyde dissolved in the mother liquor are contained in large quantities in the leaching zone, and a sufficient purifying effect by the leaching treatment cannot be obtained. Furthermore, these impurities undergo condensation to accelerate coloration. If the proportion of the mother liquor separated exceeds 98% by weight, long periods of time are required for the separation, and clogging of the discharge portion from a liquid cyclone tends to occur.

The mother liquor separated by the above procedure is recycled to the oxidation zone. If a large quantity of water is present in the mother liquor, water may be removed by distillation until the water concentration of the mother liquor reaches a moderate range. The residue may be recycled after replenishing the catalyst components.

When the oxidation reaction is carried out in an oxidation reactor having a distillation tower directly connected to its top portion so as to remove the byproduct water by distillation and maintain the water concentration of the mother liquor within the reaction system within a certain definite range, the mother liquor separated by step (B) can be directly recycled to the oxidation reactor without dehydrating it in a distillation tower provided outside the reaction system.

Separation of the mother liquor from the oxidation reaction mixture may be performed by a centrifugal method using a centrifugal separator, a liquid cyclone, or the like. The use of the liquid cyclone is preferred because it can perform separation easily at high temperatures and pressures. This separation by a liquid cyclone can be conveniently carried out, for example, by employing a process for treatment by a liquid cyclone for the production of a suspension of terephthalic acid having a reduced impurity content which comprises supplying a fresh and hot lower aliphatic carboxylic acid solvent to a liquidphase catalytic oxidation product of a p-alkylbenzene or a hot, impurity-containing suspension of terephthalic acid particles in a mother liquor containing a lower aliphatic carboxylic acid solvent, feeding the resulting mixture into a liquid cyclone, treating it in the cyclone at an elevated temperature, withdrawing an impuritycontaining liquid composed mainly of acid mother liquor from a withdrawal opening provided near one end of the cyclone, and withdrawing a suspension of terephthalic acid particles in a lower aliphatic carboxylic acid solvent consisting mainly of said fresh solvent from a withdrawal opening provided near the other end of the cyclone; wherein a fresh lower aliphatic carboxylic acid solvent is additionally supplied into the cyclone through an opening provided between a position apart from the suspension withdrawal opening of the liquid cyclone toward its mixture-feeding opening by a distance corresponding about two-thirds of the distance ($h_o$) from the mixture-feeding opening to the suspension withdrawal opening and a position apart from the suspension withdrawal opening toward its mixture feeding opening by a distance corresponding to about one-tenth of the distance ($h_o$).

According to the above preferred embodiment, the steps (B) and (C) of the process of this invention can be performed successively by a liquid cyclone.

Hot acetic acid is added to the remainder of the oxidation reaction mixture obtained in step (B) so as to form a suspension of crude terephthalic acid in hot acetic acid. Specifically, the hot acetic acid is added so that the weight ratio of acetic acid in the mixture to the crude terephthalic acid in the mixture is from 2 to 10, preferably from 3 to 8. Thus, a suspension of the crude terephthalic acid in acetic acid kept at a temperature above the oxidation reaction temperature (T) and up to about 240° C. Preferably, the hot acetic acid used in the formation of such a suspension of crude terephthalic acid is a part of acetic acid refluxed from a reflux condenser when an oxidation reactor having this reflux condenser connected to its top portion is used, or a part of acetic acid refluxed from the bottom of a distillation tower or acetic acid withdrawn from the side of the distillation tower when an oxidation reactor having the distillation tower connected to its top portion. Use of the latter method is especially preferred because acetic acid having a water content suitable for the leaching treatment can be obtained by properly choosing the position at which acetic acid is withdrawn from the distillation tower.

Thus, in accordance with one preferred embodiment of this invention, a distilling zone is provided at the top portion of the liquid-phase catalytic oxidation reaction zone, and the oxidation reaction is performed in step (A) while distilling off the by-product water from the reaction zone in the distillation zone and recycling acetic acid withdrawn from the bottom of the distilling zone to the reaction zone. In the meantime, acetic acid or water-containing acetic acid is withdrawn from the bottom or side of the distillation zone and used as the hot acetic acid in step (C).

The suspension of crude terephthalic acid in hot acetic acid which is formed in step (C) is subjected to primary leaching treatment in step (D) by stirring it at a temperature of from the oxidation reaction temperature (T) and up to about 240° C., preferably from (T+10)° C. to about 230° C. If the primary leaching temperature is lower than T° C., a sufficient purifying effect cannot be achieved. If it is higher than about 240° C., the resulting terephthalic acid has a poor optical density and it is difficult to obtain terephthalic acid having such a good quality as to give polyethylene terephthalate of good color by the direct polymerization method. When the weight ratio of acetic acid to crude terephthalic acid is less than 2, the desired purifying effect is difficult to obtain. If it exceeds 10, a further increase in purifying effect cannot be expected, and the use of too much hot acetic acid for the formation of the suspension is commercially disadvantageous. The water content of the acetic acid solvent in the suspension to be submitted to the primary leaching treatment is preferably about 3 to about 25% by weight, more preferably about 5 to about 20% by weight, based on the weight of the acetic acid solvent.

To obtain an especially good purifying effect by the primary leaching treatment of the suspension of crude terephthalic acid in acetic acid in the process of this invention, the ratio of acetic acid to the crude terephthalic acid in the suspension, and the treating temperature should be within the ranges specified hereinabove. The ratio of acetic acid solvent to crude terephthalic acid in the suspension, the treating temperature, and the water content of the acetic acid solvent are interrelated to one another and affect the purification of crude terephthalic acid. To obtain a better purifying effect, the primary leaching treatment should preferably be carried out such that the ratio of acetic acid solvent to crude terephthalic acid and the treating temperature are within the above-specified ranges, and the following equation is satisfied:

$$3.38 \geq (m+99) \times 10^{-4} t + \log x - 0.06 \log m \geq 2.78$$

wherein t is the absolute value of the temperature (°C.) at which the primary leaching treatment is performed, x is the weight ratio of the acetic acid solvent to crude terephthalic acid, and m is the absolute value of the water content (% by weight) of the acetic acid solvent.

In the process of this invention, the primary leaching treatment (D) is carried out with stirring. The intensity of stirring at this time can be chosen properly. To achieve an especially good effect by the primary leaching treatment, the stirring in step (D) is carried out under such conditions that the stirring power is at least 1 HP, for example 1 to 10 HP, preferably 1.3 to 4 HP, and the linear velocity of the tip of a stirring blade of the stirrer is at least 0.8 m/sec., for example 0.8 to 7 m/sec., preferably 1.3 to 5 m/sec.

By employing the above stirring conditions in addition to the temperature conditions, a further improvement can be achieved in step (D). The time required for the primary leaching treatment can be suitably changed. For example, the treating time is about 20 minutes to about 2 hours.

By the primary leaching treatment in step (D), oxidation intermediates such as 4-carboxybenzaldehyde and other impurities such as colored substances in the crude terephthalic acid can be selectively extracted into the acetic acid solvent.

The resulting suspension of terephthalic acid in acetic acid is then subjected to a secondary leaching treatment in step (E). The secondary leaching treatment is carried out at a temperature at least 10° C. below the primary leaching treatment temperature and within about 150° to about 220° C., thereby producing terephthalic acid crystals which are spherical in shape, have a large particle diameter, and give a slurry of good pumpability with ethylene glycol without again having the above impurities occluded in the terephthalic acid.

The temperature at which the secondary leaching treatment is carried out is more preferably at least 20° C. lower than the primary leaching treatment temperature and within about 160° C to about 200° C.

If the temperature of the secondary leaching treatment is lower than about 150° C., it is impossible to obtain terephthalic acid crystals which are spherical in shape, have a large particle diameter and give a slurry of good pumpability with ethylene glycol. In addition, the content of impurities such as 4-carboxybenzaldehyde in the resulting terephthalic acid increases. If the secondary leaching treatment temperature exceeds about 220° C., spherical terephthalic acid crystals having a large particle size and capable of giving a slurry of good pumpability with ethylene glycol cannot be obtained, and the amount of pillar-like or needle-like crystals of fine sizes increases. Furthermore, when the temperature of the secondary leaching treatment is within the specifified range but the difference between it and the primary leaching treatment temperature is less than 10° C., it is also difficult to obtain terephthalic acid having the aforesaid good shape and large particle diameter and capable of giving a slurry of good pumpability with ethylene glycol.

The secondary leaching treatment in step (E) is carried out with stirring. The intensity of the stirring can be suitably chosen. To obtain an especially good effect by the secondary leaching treatment, the stirring is suitably performed under such conditions that the stirring power is at least 1 to 5 HP, preferably 1.3 to 3 HP, per cubic meter of the suspension treated in step (D), and the linear velocity of the tip of a stirring blade of the stirrer is 0.8 to 4 m/sec., preferably 1.3 to 3 m/sec. The time required for the secondary leaching treatment differs according to the leaching temperature, the intensity of stirring, and other conditions. Usually, it is from 20 minutes to about 2 hours, preferably about 30 minutes to about 1.5 hours.

The stirrers used in the primary and secondary leaching treatments in steps (D) and (E) may be of any desired type which is equipped with stirring blades and can be operated under the aforesaid stirring conditions, and includes, for example those of the turbine blade type or paddle type. To subject the suspension of terephthalic acid in acetic acid which has been treated in step (D) the secondary leaching treatment successively, it is necessary to lower the temperature of the system to a point at least 10° C. below the primary leaching treatment temperature. The temperature of the system can be abruptly lowered by flushing the suspension of terephthalic acid in acetic acid in the primary leaching treatment vessel into the secondary leaching treatment bath maintained at a lower pressure than the primary leaching treatment bath. It is also possible to cool the suspension gradually.

The acetic acid suspension of terephthalic acid which has been subjected to the secondary leaching treatment (E) can be subjected to conventional procedures to recover high quality terephthalic acid (step F). For example, the acetic acid suspension of terephthalic acid is taken out after rapidly cooling it by flushing under atmospheric pressure, or gradually cooling it. Terephthalic acid is separated from the suspension by a conventional solid-liquid separating means such as centrifugal separation, and as required, washed and dried to recover terephthalic acid of high quality.

The accompanying drawing shows one example of an apparatus suitable for the practice of the process of this invention described hereinabove. By referring to the drawing, one embodiment of the process of this invention is described in greater detail.

A starting mixture composed of p-xylene, an oxidation catalyst and acetic acid and air are continuously fed into an oxidation reactor 10 through lines 12 and 13, respectively. The oxidation reactor 10 is equipped with a stirrer 11. By stirring the starting mixture within the oxidation reactor at a fixed temperature (T° C.) for a fixed residence time, p-xylene is oxidized to terephthalic acid, and the resulting oxidation reaction mixture containing crude terephthalic acid becomes a suspension in acetic acid. The suspension is then sent from the oxidation reactor to a first receiver 30 through a line 14 for withdrawing the oxidation reaction mixture and a valve 15. In the first receiver 30, the suspension is maintained warm so that its temperature may not be more than 30° C. below the oxidation reaction temperature (T), preferably may not be more than 20° C. below the oxidation reaction temperature. At the same time, it is stirred by a stirrer 31. A vapor of acetic acid which is genenrated in the event that pressure decrease occurs at the time of withwithdrawing the oxidation reaction mixture from the oxidation reactor 10 into the first receiver 30 is condensed through a line 32 above the first receiver and a condenser 33, and refluxed to the first receiver 30 through a line 34. In the meantime, water formed as a by-product in the oxidation reaction together with the exhaust gas from the oxidation reactor and a vapor of acetic acid is conducted to a tray-type distillation tower 20 connected directly to the top of the oxidation reactor 10. The by-product water is thus removed by distillation utilizing the heat of reaction whereby the water concentration in the mother liquor within the oxidation reactor is maintained constant. The exhaust gas containing condensed steam from the top of the distillation tower 20 is condensed through a line 21 and a condenser 22, and the condensed water-acetic acid solution enters a condensed liquid receiver 23. A part of the water-acetic acid solution containing water as a major ingredient and present in the receiver 23 is removed from a line 26 for withdrawing the condensed water. The remainder is refluxed to the top of the distillation tower 20 through a line 24. The gas which has not been condensed by the condenser 22 is exhausted from a gas exhaust line 25.

The oxidation reaction mixture in the first receiver 30 is fed into a liquid cyclone 40 through a line 35 for withdrawing the suspension of terephthalic acid in acetic acid, a pump 36 and a line 37 for supplying a liquid cyclone. In the liquid cyclone 40, a predetermined proportion of the mother liquor in the oxidation reaction mixture is separated at a predetermined temperature. The separated mother liquor is returned to the oxidation reactor 10 through a line 41.

The remainder of the oxidation reaction mixture left after the separation of the mother liquor is withdrawn from a line 42 at the bottom of the liquid cyclone 40, and hot acetic acid containing a predetermined concentration of water is withdrawn from a line 27 at the side of the distillation tower 42. They are heated to a predetermined temperature in a heat exchanger 43, and then fed into a primary leaching treatment vessel 50 where the weight ratio of acetic acid to crude terephthalic acid in the acetic acid suspension of crude terephthalic acid and the temperature of the suspension are adjusted to certain ranges, and the suspension is stirred by a stirrer 51 to perform the primary leaching treatment.

The acetic acid suspension of crude terephthalic acid subjected to the primary leaching treatment is withdrawn from a line 52 at the bottom of the leaching vessel 50, conveyed through a valve 53, and fed from an opening 54 into a secondary leaching treatment vessel 60. In the vessel 60, the suspension is subjected to the secondary leaching treatment with stirring by a stirrer at a specified temperature lower than the temperature of the primary leaching treatment. When transferring the acetic acid suspension of terephthalic acid from the primary leaching treatment vessel to the secondary leaching treatment vessel, a reduction in pressure occurs incident to the decrease of the temperature of the suspension. At this time, a part of the acetic acid solvent in the secondary leaching treatment vessel vaporizes, and is condensed through a line 65 at the top of the secondary leaching treatment vessel, a condenser 66 and a line 67, and refluxed to the secondary leaching vessel. Accordingly, the temperature can be adjusted by adjusting the pressure of the secondary leaching treatment vessel. The suspension which has been treated in the secondary leaching treatment vessel 60 is withdrawn from a line 62 at the bottom of the vessel 60, and fed into a second receiver 70 through a valve 63 and a line 64. The pressure of the second receiver 70 is maintained usually at atmospheric pressure, and its temperature, at the boiling point of acetic acid or a lower temperature at atmospheric pressure. The acetic acid suspension of terephthalic acid in the second receiver 70 is stirred by a stirrer 71. When the acetic acid suspension of terephthalic acid is transferred from the secondary leaching treatment vessel 60 to the second receiver 70, a part of the acetic acid solvent vaporizes incident to a drop in pressure. The acetic acid which has vaporized is condensed through a line 74, a condenser 75 and a line 76, and refluxed to the second receiver 70.

The acetic acid suspension of terephthalic acid in the second receiver is fed into a centrifugal separator through a line 72 at the bottom of the second receiver, a pump 73 and a line 77. Terephthalic acid crystals having high quality are obtained from a line 81, and acetic acid solvent, from a line 82. The terephthalic acid crystals withdrawn from the centrifugal separator, if required, may be washed with acetic acid, water, and the like, and dried. The acetic acid solvent recovered from the centrifugal separator can be re-used either as such, or after being purified by distillation or the like.

According to the process of this invention, p-xylene can be oxidized under relatively mild conditions which can markedly inhibit the decomposition of acetic acid solvent so as to obtain crude terephthalic acid having a specified content of 4-carboxybenzaldehyde and a specified optical density at 340 m$\mu$, and by subjecting this crude terephthalic acid to the two-step leaching treatment process under the aforesaid specified conditions, terephthalic acid of high quality can be prepared which can be used for the production of polyesters by the direct polymerization method. Since the oxidative decomposition of acetic acid solvent during the oxidation reaction can be reduced, the process of this invention has the advantage that the cost of production is low.

The process of this invention is illustrated further by the following Examples and Comparative Examples which are performed by using an apparatus of the type shown in the accompanying drawing.

The content of 4-carboxybenzaldehyde (4-CBA) in terephthalic acid (TA) was measured by polarography.

The optical density (O.D.) of terephthalic acid was determined with light having a wavelength of 340 m$\mu$ for a 2 N aqueous solution of potassium hydroxide containing 15% by weight of terephthalic acid using a 1 cm-long cell.

The shape of terephthalic acid crystals was visually evaluated by using an optical microscope.

The average particle diameter of the terephthalic acid crystals was obtained by sieving terephthalic acid crystals by a standard sieve, plotting the particle size distribution of those crystals which have passed through the sieve vs. cumulative weight percentage (Gaudin-Schuhmann plot), and determining the particle size corresponding to a 50% cumulative weight.

Polyethylene terephthalate (PET) was prepared by placing 50 g of terephthalic acid and 75 g of ethylene glycol in a flask, esterifying them at 200° C. in a stream of nitrogen, and polycondensing the esterification product at a temperature of 285° C. and a pressure of less than 0.1 mmHg using 20 mg of antimony trioxide as a catalyst.

The color tone of polyethylene terephthalate was expressed by b value [yellow (+)−blue (−)] obtained by measuring the reflective light by a color difference meter. The color tone was better as the b value was smaller.

EXAMPLE 1

An oxidation reactor 10 equipped with a distillation tower was charged with 10.8 kg of acetic acid, 1.2 kg of water, 60 g of cobalt acetate, 30 g of manganese acetate and 31 g of tetrabromoethane. While maintaining the temperature of the reactor at 190° C. and its pressure at 11 kg/cm$^2$, a mixture consisting of p-xylene (3 kg/hr), acetic acid (15.8 kg/hr), water (2.6 kg/hr), cobalt acetate (18 hg/hr), manganese acetate (9 g/hr) and tetrabromoethane (9.3 g/hr) was continuously fed into the oxidation reactor from line 12, and in the meantime, air was fed into the reactor through line 13 at a rate of about 4.2 NM$^3$/kg-p-xylene so that the concentration of oxygen in the exhaust gas was 5%. A part of the hot acetic acid within distillation tower 20 was withdrawn through line 27 at the side of the distillation tower, and a part of the recycle liquor was withdrawn through line 26, so that the water concentration of the reaction mixture was maintained at 10% by weight. The reaction mixture was stirred with an intensity of 3 HP per m$^3$ of the mixture. At this time, the concentration of the cobalt compound in the mother liquor within the oxidation reactor was 2.0×10$^{-5}$ gram-atoms [2.0 G] determined as cobalt atom per gram of the solvent; the concentration of the manganese compound was 1.0×10$^{-5}$ gram atom [1.0 G] determined as manganese atom per gram of the solvent; and the concentration of the bromine compound was 3.0×10$^{-5}$ gram-atom determined as bromine atom per gram of the solvent. (G denotes a unit which shows 10$^{-5}$ gram-atom per gram of solvent.).

The reaction mixture was sent to a liquid cyclone 40 through line 14, valve 15 and first receiver 30 on the basis of a signal of a level meter designed so as to adjust the residence time to 1 hour. In the liquid cyclone 40, 70% by weight (8.4 kg/hr) of the mother liquor was separated. The separated mother liquor was returned to the reactor through line 41. Through line 27, 85% by weight acetic acid (14.8 kg/hr) withdrawn from the side of the distillation tower was fed into the concentrated reaction mixture. The resulting mixture is heated in a heat exchanger 43, and then fed into a first leaching treatment vessel 50. The weight ratio of solvent to terephthalic acid in this mixture was 4, and the water concentration of the solvent was 14% by weight. The primary leaching treatment bath was maintained at a temperature of 220° C. and a pressure of 18 kg/cm$^2$, and the mixture was stirred with a stirring intensity of 2.5 HP per m$^3$ of the suspension while adjusting the linear velocity of the tip of the stirring blade to 2.6 m/sec. This primary leaching treatment was performed for a residence time of 1 hour, and then the acetic acid suspension of terephthalic acid maintained at 190° C. and 8 kg/cm$^2$ was fed into a secondary leaching treatment bath 60 wherein it was stirred with a stirring intensity of 2.0 HP while adjusting the linear velocity of the tip of the stirring blade of the stirrer to 2.3 m/sec. After a residence time of 1 hour, the mixture was sent to a second receiver 70, and the pressure was released to atmospheric pressure. It was then sent to a centrifugal separator 80 to separate it into terephthalic acid crystals and the acetic acid. The terephthalic acid crystals were washed, and dried.

The resulting terephthalic acid was evaluated, and the results are shown in Table 1.

EXAMPLES 2 to 24 and Comparative Examples 1 to 13

In the continuous liquid-phase oxidation of p-xylene described in Example 1, the concentrations of the catalyst ingredients in the solvent within the oxidation reactor, the concentration of water, and the weight ratio of the solvent to p-xylene fed were changed as shown in Table 1 by changing the amounts of the cobalt, manganese and bromine compounds, acetic acid and water fed. The oxygen concentration of the exhaust gas was changed as shown in Table 1 by changing the oxidation temperature and pressure and the amount of air fed into the oxidation reactor. Otherwise, the continuous liquid-phase oxidation reaction was performed by the same procedure as in Example 1. In each run, the suspension of crude terephthalic acid as shown in Table 1 was obtained.

The suspension maintained at the temperature shown in Table 1 was sent to a liquid cyclone through line 14, valve 15 and first receiver 30, and the mother liquor in each of the proportions shown in Table 1 was separated from the suspension in the same way as in Example 1, and recycled to the oxidation reactor in the same way as in Example 1.

The hot acetic acid withdrawn from the side of the distillation tower (which had the concentration indicated in Table 1) was added in varying amounts to the concentrated reaction mixture left after the separation of the mother liquor in the liquid cyclone, thereby to change the water concentration of the solvent and the weight ratio of the solvent to crude terephthalic acid as shown in Table 1. The resulting acetic acid suspension of crude terephthalic acid were subjected to a two-step leaching treatment and post-treated in the same way as in Example 1 except that the temperatures, pressures and stirring conditions were changed as shown in Table 1.

The terephthalic acid was evaluated, and the results are shown in Table 1.

Comparative Example 14

An oxidation reactor equipped with a distillation tower was charged with 12 kg of glacial acetic acid and 1.85 kg of cobalt acetate. Feeding of air was started, and the inside of the oxidation reactor was maintained at 120° C. and 10 kg/cm$^2$.G. As a result of this operation, cobaltous acetate within the reactor changed to dark green cobaltic acetate. When the temperature of the inside of the oxidation reactor reached 120° C., a mixture consisting of p-xylene (3 kg/hr), glacial acetic acid (19.5 kg/hr) and cobalt acetate (3 kg/hr) was continuously fed into the oxidation reactor from a feed line. With stirring, air was continuously fed into the reactor through a mother feed line at the bottom of the reactor. While the liquid level within the reactor was maintained constant, p-xylene was continuously oxidized while continuously discharging the oxidation reaction mixture from a discharge port at the bottom of the oxidation reactor. At this time, the concentration of the cobalt compound in the mother liquor within the oxidation reactor was $61.8 \times 10^{-5}$ gram-atoms [61.8 G] as cobalt atom per gram of the solvent.

In order to evaluate the quality of crude terephthalic acid contained in the resulting oxidation reaction mixture, one part by weight of a sample was taken out from the oxidation reaction mixture, cooled, and separated by filtration. The sample was washed at room temperature with acetic acid and water, and dried. The resulting crude terephthalic acid sample had a 4-CBA content of 13,800 ppm, and an optical density at 340 mμ of 0.192.

The oxidation reaction mixture continuously discharged from the reactor was sent to a liquid cyclone while being maintained at 120° C., and 80% by weight (9.6 kg/hr) of the mother liquor was separated. The separated mother liquor was sent to a distillation tower provided outside the reaction zone, and the excess of water was removed from the top of this distillation tower. Acetic acid having a water content of 10% by weight was recovered by side cut. Furthermore, acetic acid containing the cobalt catalyst was recovered from the bottom of the distillation tower. After adjusting the amount of the solvent and the concentration of the cobalt catalyst, this cobalt-containing acetic acid was recycled to the oxidation reactor.

The separated crude terephthalic acid contained about 30% by weight of mother liquor. The 10% by weight acetic acid recovered by the side cut of the distillation tower was added to the crude terephthalic acid so that the weight ratio of the hydrous acetic acid to the crude terephthalic acid became b 4. 1 The mixture was then sent to a primary leaching treatment vessel, and stirred at b 24020 0 1 C. and 25 1 kg/cmhu 21 .G with a 1 hour under such stirring conditions that the intensity of stirring was 2.5 HP per m$^3$ of the suspension and the linear velocity of the tip of the stirring blade was 2.6 m/sec. After the primary leaching treatment, the acetic acid suspension of terephthalic acid was sent to a secondary leaching treatment vessel maintained at 200° C. and 10 kg/cm$^2$.G, and stirred for a residence time of 1 hour under such stirring conditions that the intensity of stirring was 2.0 HP per m$^3$ of suspension and the linear velocity of the tip of the stirring blade was 2.3 m/sec. The treated mixture was flushed into a receiver maintained at atmospheric pressure. The suspension was then centrifugally separated into terephthalic acid crystals and the acetic acid solvent. The terephthalic acid crystals were washed, and dried. The resulting terephthalic acid was evaluated, and the results are shown in Table 1.

Table 1

| Example (Ex.) or Comparative Example (CEx.) | Concentration of catalyst (G)(*1) | | | Oxidation reaction | | | | | Ratio of loss of acetic acid (*3) | Quality of Crude TA | |
|---|---|---|---|---|---|---|---|---|---|---|---|
| | | | | Oxidation conditions | | | | | | | |
| | Co | Mn | Br | Temperature (°C.) | Pressure (kg/cm$^2$.G) | Concentration of water (wt. %) | Weight ratio of solvent to p-xylene (*2) | O$_2$ concentration of the exhaust gas (%) | | 4-CBA content (ppm) | Optical Density (340 mμ) |
| Ex. 1 | 2.0 | 1.0 | 3.0 | 190 | 11 | 10 | 4 | 5 | 1.00 | 900 | 0.097 |
| Ex. 2 | 1.6 | 0.8 | 2.4 | 210 | 15 | 10 | 4 | 7 | 1.25 | 600 | 0.076 |
| Ex. 3 | 1.6 | 0.008 | 2.4 | 190 | 11 | 10 | 4 | 5 | 0.88 | 1300 | 0.125 |
| Ex. 4 | 2.0 | 0.5 | 3.0 | 180 | 10 | 10 | 4 | 2 | 0.75 | 2500 | 0.200 |
| CEx. 1 | 2.0 | 0.2 | 3.0 | 240 | 25 | 10 | 4 | 5 | 1.88 | 200 | 0.055 |
| CEx. 2 | 1.8 | 0.09 | 3.0 | 200 | 12 | 10 | 4 | 5 | 1.63 | 400 | 0.073 |
| CEx. 3 | 3.0(*4) | 0.75 | 4.0(*4) | 160 | 7 | 10 | 4 | 5 | 0.63 | 3200 | 0.347 |
| CEx. 4 | 2.0 | 1.0 | 3.0(*4) | 180 | 10 | 10 | 4 | 5 | 0.75 | 2200 | 0.328 |
| CEx. 5 | 1.2 | 0.12 | 1.8 | 220 | 18 | 10 | 4 | 2 | 1.38 | 600 | 0.310 |
| CEx. 6 | 3.0 | 0.5 | 3.5 | 160 | 7 | 10 | 4 | 7 | 0.63 | 3400 | 0.280 |
| CEx. 7 | 2.0 | 1.0 | 3.0 | 190 | 11 | 10 | 4 | 5 | 1.00 | 900 | 0.097 |
| Ex. 5 | 2.0 | 1.0 | 3.0 | 190 | 11 | 10 | 4 | 5 | 1.00 | 900 | 0.097 |
| Ex. 6 | 2.0 | 1.0 | 3.0 | 190 | 11 | 10 | 4 | 5 | 1.00 | 900 | 0.097 |
| CEx. 8 | 2.0 | 1.0 | 3.0 | 190 | 11 | 10 | 4 | 5 | 1.00 | 900 | 0.097 |
| Ex. 7 | 2.0 | 1.0 | 3.0 | 190 | 11 | 10 | 4 | 5 | 1.00 | 900 | 0.097 |
| Ex. 8 | 2.0 | 1.0 | 3.0 | 190 | 11 | 10 | 4 | 5 | 1.00 | 900 | 0.097 |
| Ex. 9 | 2.0 | 1.0 | 3.0 | 190 | 11 | 10 | 4 | 5 | 1.00 | 900 | 0.097 |
| CEx. 9 | 2.0 | 1.0 | 3.0 | 190 | 11 | 10 | 4 | 5 | 1.00 | 900 | 0.097 |
| Ex. 10 | 2.0 | 1.0 | 3.0 | 190 | 11 | 10 | 4 | 5 | 1.00 | 900 | 0.097 |

Table 1-continued

| | | | | | | | | | | | |
|---|---|---|---|---|---|---|---|---|---|---|---|
| Ex. 11 | 2.0 | 1.0 | 3.0 | 190 | 11 | 10 | 4 | 5 | 1.00 | 900 | 0.097 |
| Ex. 12 | 2.0 | 1.0 | 3.0 | 190 | 11 | 10 | 4 | 5 | 1.00 | 900 | 0.097 |
| Ex. 13 | 2.0 | 1.0 | 3.0 | 190 | 11 | 10 | 4 | 5 | 1.00 | 900 | 0.097 |
| CEx. 10 | 1.6 | 0.008 | 2.4 | 190 | 11 | 10 | 4 | 5 | 0.88 | 1300 | 0.125 |
| Ex. 14 | 1.6 | 0.008 | 2.4 | 190 | 11 | 10 | 4 | 5 | 0.88 | 1300 | 0.125 |
| Ex. 15 | 1.6 | 0.008 | 2.4 | 190 | 11 | 10 | 4 | 5 | 0.88 | 1300 | 0.125 |
| CEx. 11 | 1.6 | 0.008 | 2.4 | 190 | 11 | 10 | 4 | 5 | 0.88 | 1300 | 0.125 |
| CEx. 12 | 2.0 | 1.0 | 3.0 | 190 | 11 | 10 | 4 | 5 | 1.00 | 900 | 0.097 |
| Ex. 16 | 2.0 | 1.0 | 3.0 | 190 | 11 | 10 | 4 | 5 | 1.00 | 900 | 0.097 |
| Ex. 17 | 2.0 | 1.0 | 3.0 | 190 | 11 | 10 | 4 | 5 | 1.00 | 900 | 0.097 |
| CEx. 13 | 2.0 | 1.0 | 3.0 | 190 | 11 | 10 | 4 | 5 | 1.00 | 900 | 0.097 |
| Ex. 18 | 2.0 | 1.0 | 3.0 | 190 | 11 | 10 | 4 | 5 | 1.00 | 900 | 0.097 |
| Ex. 19 | 2.0 | 1.0 | 3.0 | 190 | 11 | 10 | 4 | 5 | 1.00 | 900 | 0.097 |
| Ex. 20 | 2.0 | 1.0 | 3.0 | 190 | 11 | 10 | 4 | 5 | 1.00 | 900 | 0.097 |
| Ex. 21 | 2.0 | 1.0 | 3.0 | 190 | 11 | 10 | 4 | 5 | 1.00 | 900 | 0.097 |
| Ex. 22 | 1.6 | 0.008 | 2.4 | 190 | 11 | 10 | 4 | 5 | 0.88 | 1300 | 0.125 |
| Ex. 23 | 1.6 | 0.008 | 2.4 | 190 | 11 | 10 | 4 | 5 | 0.88 | 1300 | 0.125 |
| Ex. 24 | 1.6 | 0.008 | 2.4 | 190 | 11 | 10 | 4 | 5 | 0.88 | 1300 | 0.125 |
| CEx. 14 | 61.8 | — | — | 120 | 10 | 5 | 4 | 5 | 0.52 | 13800 | 0.192 |

| Example (Ex.) or Comparative Example (CEx.) | Conditions for separating mother liquor | | Conditions for solvent | | leaching treatment conditions | | | | | | | |
|---|---|---|---|---|---|---|---|---|---|---|---|---|
| | | | | | Primary leaching treatment | | | | Secondary leaching treatment | | | |
| | Temperature (°C.) | Proportion of mother liquor separated (wt. %) | Water content of hot acetic acid (wt. %) | Weight ratio of solvent to TA | Water content of the solvent (wt. %) | Temperature (°C.) | Pressure (kg/cm$^2$·G) | Stirring Conditions | | Temperature (°C.) | Pressure (kg/cm$^2$·G) | Stirring Conditions | |
| | | | | | | | | Power (HP/m$^3$) | Linear velocity (m/sec.) | | | Power (HP/m$^3$) | Linear velocity (m/sec.) |
| Ex. 1 | 190 | 70 | 15 | 4 | 14 | 220 | 18 | 2.5 | 2.6 | 190 | 8 | 2.0 | 2.3 |
| Ex. 2 | 200 | 60 | 10 | 5 | 10 | 220 | 18 | 2.5 | 2.6 | 190 | 8 | 2.0 | 2.3 |
| Ex. 3 | 190 | 80 | 15 | 8 | 15 | 210 | 15 | 2.5 | 2.6 | 160 | 5 | 2.0 | 2.3 |
| Ex. 4 | 180 | 90 | 20 | 8 | 20 | 210 | 15 | 2.5 | 2.6 | 160 | 5 | 2.0 | 2.3 |
| CEx. 1 | 240 | 70 | 15 | 6 | 14 | 230 | 20 | 2.5 | 2.6 | 200 | 10 | 2.0 | 2.3 |
| CEx. 2 | 200 | 80 | 15 | 4 | 14 | 220 | 18 | 2.5 | 2.6 | 180 | 7 | 2.0 | 2.3 |
| CEx. 3 | 160 | 90 | 5 | 10 | 5 | 230 | 20 | 2.5 | 2.6 | 200 | 10 | 2.0 | 2.3 |
| CEx. 4 | 180 | 90 | 20 | 8 | 20 | 220 | 18 | 2.5 | 2.6 | 190 | 8 | 2.0 | 2.3 |
| CEx. 5 | 190 | 70 | 15 | 4 | 14 | 220 | 18 | 2.5 | 2.6 | 190 | 8 | 2.0 | 2.3 |
| CEx. 6 | 160 | 90 | 20 | 8 | 20 | 210 | 15 | 2.5 | 2.6 | 190 | 8 | 2.0 | 2.3 |
| CEx. 7 | 155 | 70 | 15 | 4 | 14 | 220 | 18 | 2.5 | 2.6 | 190 | 8 | 2.0 | 2.3 |
| Ex. 5 | 170 | 70 | 15 | 4 | 14 | 220 | 18 | 2.5 | 2.6 | 190 | 8 | 2.0 | 2.3 |
| Ex. 6 | 180 | 70 | 15 | 4 | 14 | 220 | 18 | 2.5 | 2.6 | 190 | 8 | 2.0 | 2.3 |
| CEx. 8 | 190 | 50 | 15 | 6 | 14 | 220 | 18 | 2.5 | 2.6 | 180 | 7 | 2.0 | 2.3 |
| Ex. 7 | 190 | 60 | 15 | 6 | 14 | 220 | 18 | 2.5 | 2.6 | 180 | 7 | 2.0 | 2.3 |
| Ex. 8 | 190 | 80 | 15 | 6 | 14 | 220 | 18 | 2.5 | 2.6 | 180 | 7 | 2.0 | 2.3 |
| Ex. 9 | 190 | 90 | 15 | 6 | 14 | 220 | 18 | 2.5 | 2.6 | 180 | 7 | 2.0 | 2.3 |
| CEx. 9 | 190 | 70 | 15 | 1.5 | 14 | 230 | 20 | 2.5 | 2.6 | 200 | 10 | 2.0 | 2.3 |
| Ex. 10 | 190 | 70 | 15 | 3 | 14 | 230 | 20 | 2.5 | 2.6 | 200 | 10 | 2.0 | 2.3 |
| Ex. 11 | 190 | 70 | 15 | 4 | 14 | 230 | 20 | 2.5 | 2.6 | 200 | 10 | 2.0 | 2.3 |
| Ex. 12 | 190 | 70 | 15 | 6 | 14 | 200 | 13 | 2.5 | 2.6 | 180 | 7 | 2.0 | 2.3 |
| Ex. 13 | 190 | 70 | 15 | 8 | 14 | 200 | 13 | 2.5 | 2.6 | 180 | 7 | 2.0 | 2.3 |
| CEx. 10 | 190 | 80 | 15 | 8 | 15 | 180 | 7 | 2.5 | 2.6 | 160 | 5 | 2.0 | 2.3 |
| Ex. 14 | 190 | 80 | 15 | 8 | 15 | 200 | 13 | 2.5 | 2.6 | 160 | 5 | 2.0 | 2.3 |
| Ex. 15 | 190 | 90 | 10 | 6 | 10 | 230 | 20 | 2.5 | 2.6 | 200 | 10 | 2.0 | 2.3 |
| CEx. 11 | 190 | 90 | 10 | 6 | 10 | 250 | 23 | 2.5 | 2.6 | 200 | 10 | 2.0 | 2.3 |
| CEx. 12 | 190 | 70 | 15 | 4 | 14 | 230 | 20 | 2.5 | 2.6 | 230 | 14 | 2.0 | 2.3 |
| Ex. 16 | 190 | 70 | 15 | 4 | 14 | 230 | 20 | 2.5 | 2.6 | 180 | 7 | 2.0 | 2.3 |
| Ex. 17 | 190 | 70 | 15 | 4 | 14 | 230 | 20 | 2.5 | 2.6 | 160 | 5 | 2.0 | 2.3 |

Table 1-continued

| | | | | | | | | | | | | | |
|---|---|---|---|---|---|---|---|---|---|---|---|---|---|
| CEx. 13 | 190 | 70 | 15 | 4 | 14 | 230 | 20 | 2.5 | 2.6 | 140 | 5 | 2.0 | 2.3 |
| Ex. 18 | 190 | 70 | 15 | 6 | 5 | 200 | 13 | 2.5 | 2.6 | 180 | 7 | 2.0 | 2.3 |
| Ex. 19 | 190 | 70 | 15 | 6 | 10 | 200 | 13 | 2.5 | 2.6 | 180 | 7 | 2.0 | 2.3 |
| Ex. 20 | 190 | 70 | 15 | 6 | 14 | 200 | 13 | 2.5 | 2.6 | 180 | 7 | 2.0 | 2.3 |
| Ex. 21 | 190 | 70 | 15 | 6 | 20 | 200 | 13 | 2.5 | 2.6 | 180 | 7 | 2.0 | 2.3 |
| Ex. 22 | 190 | 90 | 10 | 6 | 10 | 230 | 20 | 1.3 | 1.3 | 200 | 10 | 2.0 | 2.3 |
| Ex. 23 | 190 | 90 | 10 | 6 | 10 | 230 | 20 | 4.0 | 3.9 | 200 | 10 | 2.0 | 2.3 |
| Ex. 24 | 190 | 90 | 10 | 6 | 10 | 230 | 20 | 2.5 | 2.6 | 200 | 10 | 3.0 | 2.8 |
| CEx. 14 | 120 | 80 | 10 | 4 | 10 | 240 | 25 | 2.5 | 2.6 | 200 | 10 | 2.0 | 2.3 |

| Example (Ex.) or Comparative Example (CEx.) | 4-CBA content (ppm) | Optical density (340 mµ) | Quality of TA product Average particle diameter (µ) | Shape | b-Value of PET |
|---|---|---|---|---|---|
| Ex. 1 | 300 | 0.032 | 150 | Spherical | 2.8 |
| Ex. 2 | 130 | 0.022 | 140 | " | 2.3 |
| Ex. 3 | 320 | 0.046 | 145 | " | 2.8 |
| Ex. 4 | 400 | 0.056 | 140 | " | 2.9 |
| CEx. 1 | 110 | 0.046 | 110 | " | 3.8 |
| CEx. 2 | 160 | 0.048 | 160 | " | 4.5 |
| CEx. 3 | 670 | 0.222 | 95 | " | 5.0 |
| CEx. 4 | 380 | 0.201 | 95 | " | 4.5 |
| CEx. 5 | 180 | 0.155 | 150 | " | 4.8 |
| CEx. 6 | 1300 | 0.143 | 75 | " | 5.2 |
| CEx. 7 | 580 | 0.081 | 150 | " | 4.5 |
| Ex. 5 | 390 | 0.055 | 150 | " | 3.3 |
| Ex. 6 | 320 | 0.045 | 150 | " | 3.0 |
| CEx. 8 | 490 | 0.114 | 140 | " | 3.9 |
| Ex. 7 | 230 | 0.027 | 145 | " | 2.6 |
| Ex. 8 | 210 | 0.026 | 145 | " | 2.6 |
| Ex. 9 | 200 | 0.025 | 140 | " | 2.5 |
| CEx. 9 | 780 | 0.092 | 120 | Pillar | 5.5 |
| Ex. 10 | 320 | 0.036 | 135 | Sperical | 2.8 |
| Ex. 11 | 250 | 0.027 | 135 | " | 2.6 |
| Ex. 12 | 310 | 0.032 | 145 | " | 2.9 |
| Ex. 13 | 270 | 0.031 | 130 | " | 2.8 |
| CEx. 10 | 1100 | 0.120 | 90 | Pillar | 5.1 |
| Ex. 14 | 380 | 0.056 | 145 | Spherical | 2.8 |
| Ex. 15 | 270 | 0.041 | 120 | " | 2.6 |
| CEx. 11 | 220 | 0.108 | 110 | " | 5.7 |
| CEx. 12 | 500 | 0.081 | 50 | Needle | 3.1 |
| Ex. 16 | 260 | 0.029 | 140 | Spherical | 2.6 |
| Ex. 17 | 270 | 0.036 | 90 | " | 2.7 |
| CEx. 13 | 700 | 0.086 | 85 | Needle | 5.0 |
| Ex. 18 | 330 | 0.050 | 135 | Sperical | 3.0 |
| Ex. 19 | 310 | 0.046 | 130 | " | 2.8 |
| Ex. 20 | 270 | 0.031 | 130 | " | 2.8 |
| Ex. 21 | 260 | 0.041 | 120 | " | 2.9 |
| Ex. 22 | 280 | 0.045 | 130 | " | 2.7 |
| Ex. 23 | 260 | 0.040 | 120 | " | 2.6 |
| Ex. 24 | 275 | 0.041 | 110 | " | 2.7 |

Table 1-continued

| CEx. 14 | 4200 | 0.061 | 65 | " | 5.2 |
| --- | --- | --- | --- | --- | --- |

The asterisked items in Table 1 are explained as follows:
(*1): Gram-atoms of Co, Mn and Br atoms contained per gram of the reaction solvent in the reactor $10 = 1 \times 10^{-5}$ gram-atom/gram of solvent).
(*2): The ratio of the weight of the solvent in the oxidation reaction mixture withdrawn from the oxidation reactor per unit time to the weight of p-xylene fed into the oxidation reactor per unit time.
(*3): The amount of acetic acid lost by oxidation relative to the amount of terephthalic acid formed by oxidation reaction. The amount lost of acetic acid in Example 1 was taken as 1.00, and in other examples, the ratios of the loss relative to 1.00 were calculated.
(*4): CoBr$_2$ was used as a cobalt and a bromine compound.
(*5): NaBr was used as the bromine compound.

The asterisked items in Table 1 are explained as follows:

(*1): Gram-atoms of Co, Mn and Br atoms contained per gram of the reaction solvent in the reactor ($10=1\times10^{-5}$ gram-atom/gram of solvent).

(*2): The ratio of the weight of the solvent in the oxidation reaction mixture withdrawn from the oxidation reactor per unit time to the weight of p-xylene fed into the oxidation reactor per unit time.

(*3): The amount of acetic acid lost by oxidation relative to the amount of terephthalic acid formed by oxidation reaction. The amount lost of acetic acid in Example 1 was taken as 1.00, and in other examples, the ratios of the loss relative to 1.00 were calculated.

(*4): CoBr$_2$ was used as a cobalt and a bromine compound.

(*5): NaBr was used as the bromine compound.

COMPARATIVE EXAMPLE 15

An oxidation reactor equipped with a distillation tower was charged with 11.6 kg of acetic acid, 0.4 kg of water, 87.1 g of cobalt acetate, 4.0 g of manganese acetate and 130.1 g of hydrobromic acid (47% aqueous solution). While maintaining the reactor at 174° C. and 11 kg/cm$^2$, a mixture consisting of p-xylene (3 kg/hr), acetic acid (17.5 kg/hr), water (0.5 kg/hr), cobalt acetate (130.7 g/hr), manganese acetate (6.0 g/hr) and a 47% aqueous solution of hyrobromic acid (195.2 g/hr) was continuously fed into the oxidation reactor. Air was fed in the meantime into the reactor so that the oxygen concentration of the exhaust gas became 3.9%. Thus, p-xylene was continuously oxidized. The water concentration of the reaction mixture was adjusted to 3% by partly withdrawing the recycle liquid from the top of the distillation tower. The reaction mixture was discharged continuously into a receiver so that the residence time of the reaction mixture within the reactor became 48 minutes, and the liquid level of the reactor was maintained constant.

The reaction mixture was stirred at 160° C. for 1 hour in the receiver, cooled to 20° C., washed with water at 20° C., and the mother liquor was separated. The resulting terephthalic acid was re-slurried with 3 times its weight of a 95% aqueous solution of acetic acid, and heated at 160° C. for 2 hours with stirring. Then, the mother liquor was separated at 160° C., and the residue was dried. The resulting terephthalic acid was in the form of pillar-like crystals having an average particle diameter of 72 microns. A slurry prepared from the resulting terephthalic acid and ethylene glycol had poor flowability. The resulting terephthalic acid had a 4-CBA content of 395 ppm and an optical density of 0.065. Polyethylene terephthalate prepared from this terephthalic acid and ethylene glycol had a b value of 4.5.

What we claim is:

1. A process for producing terephthalic acid by oxidizing p-xylene with a molecular oxygen-containing gas in an acetic acid solvent in the presence of a catalyst containing a cobalt compound, a manganese compound and a bromine compound at a temperature of at least about 160° C. and a pressure of at least about 5 kg/cm$^2$.G in an oxidation zone, recycling a part of the mother liquor in the resulting oxidation reaction mixture to the oxidation zone, leaching the remainder of the oxidation reaction mixture with acetic acid, and recovering terephthalic acid from the treated mixture; which comprises (A) performing said liquid-phase catalytic oxidation at a temperature (T) within the range of about 170° C. to about 230° C. to form an oxidation mixture containing crude terephthalic acid having a 4-carboxybenzaldehyde content of 500 to 3,000 ppm and an optical density, measured at 340 mμ, of not more than 0.3, (B) separating about 60 to about 98% by weight of the total mother liquor from the resulting oxidation reaction mixture at a temperature of from (T−30)° C. to (T+10)° C., and recycling the separated mother liquor to the oxidation zone, (C) adding hot acetic acid to the remainder of the oxidation reaction mixture so that the weight ratio of acetic acid to crude terephthalic acid in the mixture is 2:1 to 10:1 to form a suspension of the crude terephthalic acid in acetic acid kept at a temperature ranging from the reaction temperature (T) to about 240° C., (D) stirring the suspension at a temperature of from T° C. to about 240° C. to perform a primary leaching treatment, (E) stirring the treated suspension at a temperature of 150° C. to about 220° C., said temperature being at least 10° C. lower than the temperature of the primary leaching treatment, thereby to perform a secondary leaching treatment, and (F) recovering terephthalic acid from the suspension subjected to the secondary leaching treatment.

2. The process of claim 1 wherein the stirring in step (D) is performed under such conditions that the stirring power is at least 1 HP per cubic meter of the suspension and the linear velocity of the tip of a stirring blade is at least 0.8 m/sec.

3. The process of claim 1 wherein the stirring in step (E) is performed under such conditions that the stirring power is 1 to 5 HP per cubic meter of the suspension, and the linear velocity of the tip of a stirring blade is 0.8 to 4 m/sec.

4. The process of claim 1 wherein the crude terephthalic acid in the oxidation reaction mixture of step (A) has a 4-carboxybenzaldehyde content of 600 to 2,500 ppm, and an optical density at 340 mμ of not more than 0.2.

5. The process of claim 1 wherein in step (C), the weight ratio of acetic acid to crude terephthalic acid in the product is 3:1 to 8:1, and the temperature of the acetic acid ranges from a point 10° C. above the oxidation reaction temperature to about 230° C.

6. The process of claim 1 wherein the temperature in step (E) is about 160° C. to about 200° C. and at least 20° C. below the primary leaching temperature.

7. The process of claim 1 wherein in step (D), the suspension contains about 5 to about 20% by weight, based on the weight of the mother liquor in the suspension, of water.

8. The process of claim 1 wherein in step (A), a distillation zone is provided at the top of the oxidation reaction zone, and the catalytic oxidation reaction is performed while removing by-product water from the oxidation zone by distillation and recycling the acetic acid from the bottom of the distillation zone to the oxidation zone.

9. The process of claim 8 wherein acetic acid or hydrous acetic acid is withdrawn from the bottom or side of the distillation zone, and used as the hot acetic acid in step (C).

10. The process of claim 2 wherein the stirring power is 1.3 to 4 HP, and the linear velocity of the tip of the stirring blade is 1.3 to 5 m/sec.

11. The process of claim 3 wherein the stirring power is 1.3 to 3 HP and the linear velocity of the tip of the stirring blade is 1.3 to 3 m/sec.

12. The process of claim 4 wherein step (B) is carried out at a temperature of from (T-20)° C. to T° C.; the weight ratio of acetic acid to crude terephthalic acid in step (C) is from 3:1 to 8:1 and the suspension of the crude terephthalic acid in acetic in step (C) is maintained at a temperature in the range from (T+10)° C. to about 230° C.; in step (D) the suspension contains about 5° to about 20° by weight; based on the weight of the mother liquor in the suspension, of water; and in step (E) the treated suspension is stirred at a temperature in the range of from about 160° C. to about 200° C., said temperature being at least about 20° C. lower than the temperature of the primary leaching treatment.

13. The process of claim 12 wherein the stirring in step (D) is performed under such conditions that the stirring power is at least 1 HP per cubic meter of the suspension and the linear velocity of the tip of a stirring blade is at least 0.8 m/sec and the stirring in step (E) is performed under such conditions that the stirring power is 1 to 5 HP per cubic meter of the suspension, and the linear velocity of the tip of a stirring blade is 0.8 to 4 m/sec.

14. The process of claim 13 wherein the stirring power in step (D) is 1.3 to 4 HP, and the linear velocity of the tip of the stirring blade is 1.3 to 5 m/sec and in step (E) the stirring power is 1.3 to 3 HP and the linear velocity of the tip of the stirring blade is 1.3 to 3 m/sec.

* * * * *